(12) United States Patent
Duran Muiños et al.

(10) Patent No.: US 10,716,750 B2
(45) Date of Patent: Jul. 21, 2020

(54) TOPICAL OPHTHALMIC FORMULATIONS OF ENDOTHELIN RECEPTOR ANTAGONISTS

(71) Applicant: Retinset, S.L., Sant Cugat del Valles (ES)

(72) Inventors: Vicente Duran Muiños, Sant Cugat del Valles (ES); Marta Guerrero Martínez, Sant Cugat del Valles (ES); Cristina Hernández Pascual, Sant Cugat del Valles (ES); José Bruno Montoro Ronsano, Sant Cugat del Valles (ES); Rafael Simó Canonge, Sant Cugat del Valles (ES); José Maria Suñé Negre, Sant Cugat del Valles (ES); José Ramón Ticó Grau, Sant Cugat del Valles (ES)

(73) Assignee: Retinset, S.L., Sant Cugat del Valles (ES)

( * ) Notice: Subject to any disclaimer, the term of this patent is extended or adjusted under 35 U.S.C. 154(b) by 0 days.

(21) Appl. No.: 15/561,922

(22) PCT Filed: Mar. 22, 2016

(86) PCT No.: PCT/ES2016/070197
§ 371 (c)(1),
(2) Date: Sep. 26, 2017

(87) PCT Pub. No.: WO2016/156639
PCT Pub. Date: Oct. 6, 2016

(65) Prior Publication Data
US 2018/0110728 A1 Apr. 26, 2018

(30) Foreign Application Priority Data
Mar. 27, 2015 (ES) .................. 201530409

(51) Int. Cl.
| | |
|---|---|
| A61K 9/00 | (2006.01) |
| A61K 47/10 | (2017.01) |
| A61K 31/506 | (2006.01) |
| A61P 27/02 | (2006.01) |
| A61K 9/06 | (2006.01) |
| A61K 9/08 | (2006.01) |
| A61K 9/127 | (2006.01) |
| A61K 45/06 | (2006.01) |
| A61K 47/02 | (2006.01) |

(52) U.S. Cl.
CPC .......... *A61K 9/0048* (2013.01); *A61K 9/0051* (2013.01); *A61K 9/06* (2013.01); *A61K 9/08* (2013.01); *A61K 9/1271* (2013.01); *A61K 31/506* (2013.01); *A61K 45/06* (2013.01); *A61K 47/02* (2013.01); *A61K 47/10* (2013.01); *A61P 27/02* (2018.01)

(58) Field of Classification Search
CPC ........ A61K 9/0048; A61K 9/08; A61K 47/02; A61K 9/1271; A61K 45/06; A61K 9/06; A61K 31/506; A61K 47/10; A61K 9/0051; A61K 31/513; A61K 31/505; A61K 31/422; A61K 31/4025; A61P 27/02
See application file for complete search history.

(56) References Cited

U.S. PATENT DOCUMENTS

| | | | | |
|---|---|---|---|---|
| 2002/0002185 A1* | 1/2002 | Reed | .................... | A61K 9/0048 514/330 |
| 2003/0176356 A1* | 9/2003 | Yorio | ................... | A61K 31/519 514/20.8 |
| 2011/0104206 A1* | 5/2011 | Nanduri | ............... | A61K 9/0019 424/239.1 |
| 2017/0065611 A1* | 3/2017 | Weiss | ................... | A61K 9/0048 |

FOREIGN PATENT DOCUMENTS

CA 2071193 12/1992

OTHER PUBLICATIONS

Chou et al. (2014) Endothelin Receptor Antagonist-A Attenuates Retinal Vascular and neuroretinal Pathology in Diabetic Mice. Invest Ophthalmol Vis 55(4):2516-2525.
International Preliminary Report on Patentability corresponding to International Application No. PCT/ES2016/070197 dated Oct. 3, 2017.
International Search Report and Written Opinion of the International Searching Authority corresponding to International Application No. PCT/ES2016/070197 dated Jul. 13, 2016.
Simé et al. (2014) Neurodegeneration in the diabetic eye: new insights and therapeutic perspectives. Trends Endocrin Metab 25(1):23-33.

* cited by examiner

*Primary Examiner* — Snigdha Maewall
(74) *Attorney, Agent, or Firm* — Jenkins, Wilson, Taylor & Hunt, P.A.

(57) ABSTRACT

The present invention relates to a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan. It also relates to the use of a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, as active ingredient for preventing and/or treating the retinal neurodegeneration induced by diabetes and/or aging.

10 Claims, No Drawings

TOPICAL OPHTHALMIC FORMULATIONS OF ENDOTHELIN RECEPTOR ANTAGONISTS

FIELD OF THE INVENTION

The present invention relates to the field of medicine and concerns topical ophthalmic formulations comprising at least one antagonist of the endothelin receptor, preferably selected from sitaxentan, ambrisentan, atrasentran, bosentan, macitentan and tezosentan, or a mixture thereof, more preferably bosentan, as active ingredient for treating ocular disorders induced by metabolic diseases, such as diabetes, and/or aging.

BACKGROUND ART

Diabetes is a chronic disease characterized by the presence of hyperglycaemia that is triggered when the body loses its ability to produce enough insulin or to use it effectively. There are two main types of diabetes: type 1 and type 2. Type 2 diabetes is the most common type of diabetes which usually occurs in adults, but there are increasingly more cases of children and teenagers.

The number of people with type 2 diabetes is rapidly increasing worldwide. This increase is associated with the economic development, which implies an increased aged population and changes in lifestyle (unhealthy diets and reduced physical activity).

Diabetes can cause serious late complications which are classified in microangiopathic (retinopathy, neuropathy and diabetic nephropathy) and macroangiopathic (cardiovascular disease).

Diabetic retinopathy (DR) is the most common complication of diabetes and the leading cause of decreased visual acuity and blindness in working-age population in developed countries. The incidence of DR increases with the time of evolution of diabetes. Thus, 90% of patients with type 1 diabetes and 60% of patients with type 2 diabetes have some degree of DR after 20 years of evolution of diabetes. The prevalence of DR in Western countries is very similar and is around 30% and in 10% of cases the DR is in advanced stages that seriously threaten vision, as described in Yau et al., *Meta-Analysis for Eye Disease (META-EYE) Study Group. Global prevalence and major risk factors of diabetic retinopathy*, Diabetes Care, 2012, 35, 556-64.

According to the *International Diabetes Federation. Diabetes Atlas (6th Edition, 2014)* (http://www.idf.org/diabetesatlas), the number of diabetic patients in the world will exponentially grow in the coming years: it is estimated that will rise from 387 million of diabetic patients in 2014 to 592,000,000 in 2035. Consequently, the number of patients with DR will also increase in parallel.

A strict control of blood glucose and blood pressure are essential for preventing or slowing the progression of DR. However, the therapeutic objectives are difficult to achieve and consequently, the DR is eventually developed in a high proportion of patients.

Current treatments for DR such as laser photocoagulation, intravitreal injections of corticosteroids or blocking agents of vascular endothelial growth factor (anti-VEGF: ranibizumab, bevacizumab, pegaptanib, and aflibercept) or vitreoretinal surgery are indicated in very advanced stages of the disease, have limited effectiveness and are associated with significant adverse effects. Thus, the laser treatment is associated with a moderate vision loss, a reduced field of view, a reduced colour vision, and a reduction in contrast sensitivity. Intravitreal injections involve adverse effects such as infections, glaucoma and cataract formation and, since they must be repeatedly administered, the risk of occurrence of side effects is multiplied. In addition to the adverse local effects, anti-VEGF agents can also cause systemic complications due to its ability to pass into the systemic circulation. In short, current treatments for DR are only applicable in the advanced stages of the disease and are associated with significant adverse effects.

The DR has traditionally been considered as a microcirculatory disease of the retina. However, as described in Lieth et al., *Retinal neurodegeneration. Early pathology in diabetes*, Clin. Exper. Ophthalmol., 2000, 28: 3-8, there is increasing evidence, based on neurophysiological, psychometric, histopathologic and biochemical observations, suggesting that retinal neurodegeneration is an early event in the pathogenesis of DR which participates in the microcirculatory abnormalities that occur in DR. Thus, the main features of retinal neurodegeneration (apoptosis and glial activation) have been detected in the retinas from diabetic donors who had no microvascular alterations. Clinically, retinal neurodegeneration produces functional abnormalities, such as loss of colour discrimination and of contrast sensitivity. These alterations can be detected in diabetic patients before injuries are observed in fundus examination.

In the review article Simó et al., *Neurodegeneration in the diabetic eye: new insights and therapeutic perspectives*, Trends Endocrin. Metab., 2014, 25, 23-33, it is disclosed that treatments based on neuroprotection open a new approach to prevent or stop the development of DR. In this article some strategies are described which are in the experimental stage, but clinical trials supporting the efficacy and safety of these therapeutic approaches are not available yet.

In the article by Chou et al., *Endothelin Receptor Antagonist-A Attenuates Retinal Vascular and neuroretinal Pathology in Diabetic Mice*, Invest. Ophthalmol. Vis., 2014, 55, 2516-2525, oral administration of atrasentan, a selective blocking agent of $ET_A$ receptor of endothelin 1 is disclosed, and a significant reduction of vascular and neuroretinal complications in diabetic mice was observed. Such oral administration has the disadvantage that may have associated systemic effects. Furthermore, given the existence of the blood-retinal barrier, high serum concentrations are required for achieving pharmacological concentrations in the retina.

US 2003/0176356 describes a pharmaceutical composition comprising endothelin antagonists such as bosentan, but for treating a different disease, such as glaucoma. This document discloses general formulations which have not proven their viability. Indeed, they are applied generally stating that they can be used for any inhibitor of endothelin, when the galenical practice has shown that the same formulation developed for a particular active ingredient is not suitable for other active ingredient, albeit of the same drug family, because a small change in the molecular structure thereof presupposes the modification of its pharmaceutical, chemical and physical characteristics. In this case, it can be stated that the formulations set forth therein would not allow to obtain a stable solution and viable in time, without proving their correct preparation or their viability for ophthalmic application.

Despite the solutions described in the prior art, there is an ongoing need for new pharmacological therapies for the prevention and/or treatment of DR, which avoid the systemic treatment or intravitreal injections, in order to minimize potential side effects, and to be administered easily and over long periods.

OBJECT OF THE INVENTION

The object of the invention is the use of a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, as active ingredient for manufacturing a medicament for the prevention and/or treatment of the retinal neurodegeneration induced by diabetes and/or aging, or, a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, as active ingredient for use in the prevention and/or treatment of the retinal neurodegeneration induced by diabetes and/or aging, or, a method of prevention and/or treatment of the retinal neurodegeneration induced by diabetes and/or aging comprising administering a therapeutically effective amount of a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, as active ingredient.

Another object of the invention is a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan.

DETAILED DESCRIPTION OF INVENTION

The object of the present invention is the use of a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, as active ingredient for manufacturing a medicament for the prevention and/or treatment of the retinal neurodegeneration induced by diabetes and/or aging.

The invention further relates to a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, ingredient for use in the prevention and/or treatment of the retinal neurodegeneration induced by diabetes and/or aging.

The invention also relates to a method of treatment of the retinal neurodegeneration induced by diabetes and/or aging comprising administering a therapeutically effective amount of a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, as active ingredient according to the different embodiments disclosed herein.

The term "therapeutically effective amount" relates to an amount or dosage of an active compound(s) or composition disclosed herein which will lead to one or more desired effects, in particular therapeutic effects. An effective amount or a therapeutically effective amount of a substance may vary according to factors such as the disease state, age, sex and weight of the individual, and the ability of the substance to elicit a desired response in the individual. The dosage regimen may be adjusted to provide the optimal therapeutic response (such as, prolonged beneficial effects). For example, several daily divided doses may be administered or the dose may be proportionally reduced as indicated by the exigencies of the therapeutic situation.

The authors of the present invention have found that a topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, as active ingredient, surprisingly, prevents the retinal neurodegeneration induced by diabetes and it is suitable for the treatment in the early stages of said neurodegeneration. Said formulation allows the active ingredient to penetrate into the ophthalmic mucosa until reaching the retina, where it acts therapeutically.

Although the topical ocular route is not considered as a suitable route of administration for treating DR, because it is considered that drugs administered by this route do not reach the retina, the performed tests show that the formulation of the present invention reaches the retina and prevent neurodegeneration thereof.

In the present description and claims, the singular forms "a", "an" and "the" include plural reference unless the context clearly indicates otherwise.

In the present description the percentages are expressed in weight/volume (w/v) percentage, unless otherwise is clearly indicated.

Retinal Neurodegeneration

From the histological point of view, retinal neurodegeneration is characterized by activation of glial cells (reactive gliosis) and apoptotic death of neurons, particularly neurons of ganglion cell layer.

The main clinical manifestations of retinal neurodegeneration are defects in contrast sensitivity and visual fields, as well as the difficulty of dark adaptation, as disclosed by Di Leo et al., *Presence and further development of retinal dysfunction after 3-year follow up in IDDM patients without angiographically documented vasculopathy, Diabetologia*, 1994, 37, 911-916, and by Frost-Larsen et al., Value of electroretinography and dark adaptation as prognostic tools in diabetic retinopathy, Dev. Ophthalmol., 1981, 2, 222-234. From a clinical point of view, it is important to early identify the neurodegeneration in order to start a treatment based on drugs with neuroprotective effect.

The early stages of retinal neurodegeneration can be detected by an eye examination using the frequency domain optical coherence tomography (FD-OCT) or multifocal electroretinogram (mfERG) as described in Simo et al., *op. cit.* These scans are not included among the routine eye exams performed periodically on diabetic patients to diagnose DR, since there are currently no treatments for DR based on neuroprotection.

Preferably, the use of the topical ophthalmic formulation comprising at least one antagonist of the endothelin receptor, preferably selected from sitaxentan, ambrisentan, atrasentran, bosentan, macitentan and tezosentan, or a mixture thereof, more preferably bosentan, is for preventing and/or treating retinal neurodegeneration induced by diabetes.

Preferably, said use is for preventing and/or treating the early stages of retinal neurodegeneration induced by diabetes and/or aging.

Preferably, said use is for preventing and/or treating the early stages of retinal neurodegeneration induced by diabetes.

The Topical Ophthalmic Formulation

The topical ophthalmic formulation of the present invention can be in liquid, semisolid or solid pharmaceutical form. The liquid pharmaceutical form can be, for example, a solution, suspension, fluid emulsion, fluid gel, microemulsion, nanoemulsion, or colloidal system. The semisolid pharmaceutical form can be, for example, an ointment, cream, unguent, gel, or paste. The solid pharmaceutical form can be, for example, an ophthalmic implant, poultice, or bandage.

In a preferred embodiment, the topical ophthalmic formulation is a liquid pharmaceutical form, more preferably an aqueous solution.

In a further preferred embodiment, the topical ophthalmic formulation is an aqueous solution comprising:
1) bosentan as active ingredient,
2) a pharmaceutically acceptable wetting solvent selected from the group consisting of polyethylene glycol (PEG), propylene glycol, glycerine, and mixtures thereof, and/or a solubilizer selected from the group consisting of polyoxyethylenated derivatives of castor oil (they are commercially available, for example, under the name Cremophor® RH40 supplied by BASF), polyoxyethylenated stearates, polyethylene glycol, polysorbates, poloxamers, glycerine, medium chain $C_6$-$C_{10}$ triglycerides, and mixtures thereof;
3) a pharmaceutically acceptable pH buffer system to adjust an aqueous solution at a pH between 3.5 and 10.5.

Said aqueous solution comprises water as a solvent.

The Active Ingredient

The active ingredient of the present invention is at least one antagonist of the endothelin receptor, preferably selected from sitaxentan, ambrisentan, atrasentran, bosentan, macitentan and tezosentan, or a mixture thereof.

More preferably, in the formulation of the present invention the active ingredient is 4-(1,1-dimethylethyl)-N-[6-(2-hydroxyethoxy)-5-(2-methoxyphenoxy)[2,2'-bipyrimidin]benzenesulfonamide, which corresponds to the international common name for bosentan.

The preparation of bosentan is described in the Canadian Patent Application CA-A-2071193 by Hoffmann-La Roche and is one antagonist of the endothelin receptor, which is used in medicine as antihypertensive agent, especially in the treatment of pulmonary arterial hypertension.

In the context of the present invention the term "bosentan" refers to bosentan, to hydrates and salts thereof, such as bosentan monohydrate or sodium salt of bosentan. In the formulation of the present invention, bosentan monohydrate is preferably used.

In a formulation of the present invention, bosentan, expressed as bosentan, is generally present between 0.1% and 5% (w/v) relative to the total volume of the formulation, preferably between 0.2% and 2% and even more preferably between 0.5% and 1%. In case of using bosentan as the monohydrate or other hydrate, or as sodium salt or another salt, the skilled person can easily calculate the corresponding amounts.

In the formulation of the present invention, the active ingredient can be found incorporated in the form of microparticles, nanoparticles, liposomes or niosomes.

In a preferred embodiment, the formulation of the present invention comprises bosentan in combination with another active ingredient, for example, steroids, prostaglandins, growth factors, anti-VEGF factors or peptides. Preferably, bosentan is used in combination with growth factors.

The Wetting Solvent

The formulation of the present invention comprises a pharmaceutically acceptable wetting solvent selected from the group consisting of polyethylene glycol, propylene glycol, glycerine, and mixtures thereof.

A wetting solvent, in the context of the present invention, is a compound having solvent and wetting properties.

Among them is the polyethylene glycol (PEG), name designating a large family of polymers with different molecular weights, obtained by condensation of ethylene oxide and water in the presence of a catalyst. The formula of these polymers can be represented as $H(OCH_2CH_2)_nOH$, wherein n represents the average number of oxyethylene groups.

PEG is widely used in pharmaceutical compositions, including parenteral, topical, ophthalmic, oral, and rectal formulations, since it is a stable compound which is essentially non-irritating to the skin. Furthermore, it is a readily water soluble hydrophilic compound.

The proper PEG for use in the formulation of the present invention can have a molecular weight from 300 to 35000, preferably from 600 to 20000, more preferably from 1000 to 8000, even more preferably from 3000 to 6000, and still more preferably about 4000. The different PEGs are designated by a number that accompanies the term PEG. Thus PEG 200 means a PEG having an average molecular weight of about 200. Depending on the molecular weight PEG is liquid or solid. Thus, PEG with an average molecular weight of up to 800 are liquid at room temperature, PEG 1000 melts at a temperature between 37° C. and 40° C., and PEG 4000 melts between 50° C. and 58° C. The higher ethylene oxide content, the higher the melting point of PEG.

PEG is commercially available, for example under the name Carbowax supplied by Dow Chemical Company.

Propylene glycol is a transparent, viscous, colourless and practically odourless liquid obtained by hydrolysis of propylene oxide.

Glycerine is also a colourless, transparent, viscous, and practically odourless liquid with a slightly sweet taste.

In the formulation of the present invention, PEG and/or propylene glycol are used as wetting solvent, more preferably PEG 4000 and/or propylene glycol, and still more preferably PEG 4000.

In the formulation of the present invention the content of wetting solvent is usually between 1% and 49% (w/v) relative to the total volume of the formulation, preferably between 5% and 40%, more preferably between 10% and 30%, and even more preferably between 15% and 25%.

pH Buffer System

The formulation of the present invention comprises a pharmaceutically acceptable buffer system for adjusting the pH of the aqueous solution to a value between 3.5 and 10.5, preferably between 4.0 and 8.5, more preferably between 6.0 and 8.2, more preferably between 7.0 and 8.1, and even more preferably between 7.5 and 8.0.

The appropriate buffer system for obtaining such pH may be selected by the person skilled in the art among the buffer systems used in pharmaceutical formulations such as, citric/citrate buffers, phosphate buffer solutions, boric-borate buffer solutions, and mixtures thereof. Said buffer system may include amino acids and/or aminated substances.

In the formulation of the present invention, the pH buffer system is preferably selected from the buffer system consisting of boric acid, glycine and an amine selected from the group consisting of trometamol, arginine, lysine, methylglucamine, and mixtures thereof; citric acid/citrate system, and phosphate system. Preferably the pH buffer system consists of boric acid, glycine and an amine selected from the group consisting of trometamol, arginine, lysine, methylglucamine, and mixtures thereof; or citric acid/citrate system. More preferably the pH buffer system consists of boric acid, glycine and an amine selected from the group consisting of trometamol, arginine, lysine, methylglucamine, and mixtures thereof, and still more preferably the pH buffer system consists of boric acid, glycine and trometamol.

The amount of pH buffer system necessary to adjust the pH to the desired value is a common task that does not represent any difficulty for the person skilled in the art. In the case of a pH buffer system consisting of boric acid, glycine and an amine, usually the content of boric acid is between 0.1% and 10% (w/v) relative to the total volume of the formulation, more preferably between 0.5% and 5%, and still more preferably between 0.75% and 1.5%; the content of glycine is between 0.5% and 20% (w/v) relative to the total volume of the formulation, more preferably between 0.75% and 10%, and even more preferably between 1.5% and 2.5%; and the content of amine is between 0.1% and 25% (w/v) relative to the total volume of the formulation, preferably between 0.5% and 10%, more preferably between 0.75% and 5%, and still more preferably between 1% and 2.5%.

Other Components

The topical ophthalmic formulation of the present invention may include other components such as, for example, surfactants, cosolvents, viscosifying agents, preservatives, isotonizing agents, isoosmotizing agents, absorption enhancers of the active ingredient, mucoadhesive polymers, non-mucoadhesive polymers, chelants, stabilizers, antioxidants, and mixtures thereof.

Among surfactants there may be mentioned, for example, polyethoxylated glycerides, polysorbates, poloxamers, sodium lauryl sulphate, phospholipids, such as phosphatidylcholine or phosphatidylglycerol and their derivatives, polyoxyethylenated hydrogenated castor oil, polyoxyethylenated fatty acids, mixtures of mono-, di-, and triglycerides of fatty acids optionally polyoxyethylenated, and mixtures thereof.

Among cosolvents or solubilizers there may be mentioned, for example, polyoxyethylenated derivatives of castor oil (commercially available, for example, under the name Cremophor® RH40 supplied by BASF), polyoxyethylenated stearates, polyethylene glycol, polysorbates, poloxamers, glycerine, medium chain $C_6$-$C_{10}$ triglycerides, and mixtures thereof.

Among viscosifying agents there may be mentioned, for example, polyvinyl alcohol, methyl cellulose, hydroxypropylmethyl cellulose, carbomers, polyethylene glycol, and mixtures thereof.

Among preservatives there may be mentioned, for example, benzalkonium chloride, boric acid, benzoic acid, $C_1$-$C_4$ alkyl esters of p-hydroxybenzoic acid, chlorobutanol, benzyl alcohol, phenylethyl alcohol, organometallic derivatives of mercury, polyquaternium such as polyquaternium 1, and mixtures thereof.

Among isotonizing and isoosmotizing agents there may be mentioned, for example, inorganic salts such as sodium chloride, dextrose, trehalose, mannitol, amino acids, and mixtures thereof.

Among absorption enhancers of the active ingredient there may be mentioned, for example, saponin, fatty acid, $C_1$-$C_4$ alkyl ester of a fatty acid, pyrrolidone, polyvinylpyrrolidone, pyruvic acid, pyroglutamic acid, and mixtures thereof.

Among mucoadhesive polymers there may be mentioned, for example, hyaluronic acid, polygalacturonic acid, polyacrylic acid, carboxymethyl amylose, carboxymethyl chitin, chondroitin sulphate, methyl cellulose, gelatine, hydroxymethyl cellulose, hydroxypropyl cellulose, hydroxypropylmethyl cellulose, sodium carboxymethyl cellulose, xanthan gum, chitosan, carbopol, polycarbophil, gellan gum, carrageenan, alginates, pectin, poloxamer, and mixtures thereof.

Among non-mucoadhesive polymers there may be mentioned, for example, polyvinyl alcohol.

Among chelants there may be mentioned, for example, disodium edetate, and disodium cromoglycate.

Among stabilizers of the active ingredient there may be mentioned, for example, citric acid, ascorbic acid, glycine, arginine, lysine, and mixtures thereof.

Among antioxidants there may be mentioned, for example, sodium metabisulfite, sodium bisulfite, acetylcysteine, ascorbic acid, and mixtures thereof.

Among gelling agents there may be mentioned, for example, carbomers, methyl cellulose, hydroxypropylmethyl cellulose, poloxamers, polyacrylic acid, alginate, chitosan, xanthan gum, gellan gum, xyloglucan, and mixtures thereof.

Among excipients for emulsions and microemulsions there may be mentioned, for example, fatty acid esters and glycerine, polyoxyethylenated alcohols, polyoxyethylenated fatty acids, polyoxyethylenated derivatives of castor oil, medium chain $C_6$-$C_{10}$ triglycerides, and mixtures thereof.

Among excipients for ointments and creams there may be mentioned, for example, paraffins, high molecular weight polyethylene glycols, silicones, and mixtures thereof.

Compounds used for preparing microparticles, nanoparticles, liposomes or niosomes are, for example, polylactic acid, poly(lactic-co-glycolic) acid, polystyrenes, chitosan, albumin, gelatine, lectins, cyanoacrylates, polycaprolactones, methacrylates, polyacrylamides, alginates, dextrans, agarose, polyoxyethylene sorbitan derivatives, cholesterol, polyethoxylated fatty alcohol, dicetyl phosphate, phosphatidylcholine and mixtures thereof.

The ophthalmic formulation of the present invention can be sterile, disregarding then the above-mentioned preservatives. In this case the formulation may be prepared according to the most suitable pharmaceutical technique according to a person skilled in the art, whether by aseptic preparation, sterilizing filtration, or sterilization of the final formulation.

In a preferred embodiment, the topical ophthalmic formulation of the present invention is an aqueous solution comprising:

1) between 0.1% and 0.5% (w/v), preferably between 0.2% and 2%, and more preferably between 0.5% and 1% of bosentan;
2) between 1% and 49% (w/v), preferably between 5% and 40%, more preferably between 10% and 30% and still more preferably between 15% and 25% of wetting solvent selected from PEG and/or propylene glycol, preferably from PEG 4000 and/or propylene glycol;
3) between 0.1% and 10% (w/v), preferably between 0.2% and 5%, and more preferably between 0.5% and 1.5% of phenylethyl alcohol;
4) between 0.5% and 20% (w/v), preferably between 0.75% and 10%, and more preferably between 1.5% and 2.5% of glycine; and
5) between 0.1% and 25% (w/v), preferably between 0.5% and 10%, more preferably between 0.75% and 5%, and still more preferably between 1% and 2.5% of an amine selected from the group consisting of trometamol, arginine, lysine, methylglucamine, and mixtures thereof, preferably trometamol;

wherein the pH of the aqueous solution is comprised between 3.5 and 10.5, preferably between 4.0 and 8.5, more preferably between 6.0 and 8.2, more preferably between 7.0 and 8.1, and even more preferably between 7.5 and 8.0; and wherein the percentages (w/v) are expressed with respect to the total volume of the formulation. In another more preferred embodiment, the formulation of the present invention consists essentially of the above components with the reflected amounts, and in form of an aqueous solution.

In another preferred embodiment, the topical ophthalmic formulation of the present invention comprises:
1) between 0.1% and 0.5% (w/v), preferably between 0.2% and 2%, and more preferably between 0.5% and 1% of bosentan;
2) between 1% and 49% (w/v), preferably between 5% and 40%, more preferably between 10% and 30% and still more preferably between 15% and 25% of the solubilizer polyoxyethylenated derivative of castor oil, preferably Cremophor® RH40;
3) between 0.5% and 20% (w/v), preferably between 0.75% and 10%, and more preferably between 1.5% and 2.5% of glycine; and
4) between 0.1% and 25% (w/v), preferably between 0.5% and 10%, more preferably between 0.75% and 5%, and still more preferably between 1% and 2.5% of an amine selected from the group consisting of trometamol, arginine, lysine, methylglucamine, and mixtures thereof, preferably trometamol;

wherein the pH of the aqueous solution is comprised between 3.5 and 10.5, preferably between 4.0 and 8.5, more preferably between 6.0 and 8.2, more preferably between 7.0 and 8.1, and even more preferably between 7.5 and 8.0; and wherein the percentages (w/v) are expressed with respect to the total volume of the formulation.

In another preferred embodiment, the topical ophthalmic formulation of the present invention comprises:
1) between 0.1% and 0.5% (w/v), preferably between 0.2% and 2%, and more preferably between 0.5% and 1% of bosentan;
2) between 1% and 49% (w/v), preferably between 5% and 40%, more preferably between 10% and 30% and still more preferably between 15% and 25% of wetting solvent selected from PEG and/or propylene glycol, preferably from PEG 4000 and/or propylene glycol;
3) the citric acid/citrate system as a pH buffer system;

wherein the pH of the aqueous solution is comprised between 3.5 and 10.5, preferably between 4.0 and 8.5, more preferably between 6.0 and 8.2, more preferably between 7.0 and 8.1, and even more preferably between 7.5 and 8.0; and wherein the percentages (w/v) are expressed with respect to the total volume of the formulation. In another more preferred embodiment, the formulation of the present invention consists essentially of the above components with the reflected amounts, and in form of an aqueous solution.

Preparation Process

The process for preparing the formulation of the present invention is a standard procedure in the pharmaceutical field.

For preparing an aqueous solution, the process generally starts by introducing a part of the water in the reactor, and then the wetting solvent(s) or solubilizer(s), the components of the pH buffer system and the active ingredient are consecutively added under stirring at room temperature. The active ingredient can also be added interspersed with the components of the pH buffer system in order to facilitate dissolution. It is recommended that, after each addition, the reactor contents be agitated until complete dissolution of the added component is observed.

For preparing suspensions, ointments, creams and emulsions, and the selection of appropriate excipients, one can use the common general knowledge or pharmaceutical technology handbooks well known to a person skilled in the art, for example, *Remington: The Science and Practice of Pharmacy*, 20th edition, Lippincott, Williams & Wilkins, Philadelphia, 2000, or in the review article Souza et al, *Topical ocular delivery of therapeutics: carrier systems and physical methods*, J. Pharm. Pharmacol., 2013, 66, 507-530.

Application Assays

As disclosed in detail in the Examples section, the topical ophthalmic formulation of the present invention was administered directly into the eyes of diabetic mice (db/db).

These animals have a mutation in the gene encoding the leptin receptor and represent a model of obesity-induced type 2 diabetes as described in, for example, Duval et al., *Characterization of db/db mice for efficacy/safety pharmacology assessment of antidiabetic drugs*, Safety Pharmacology Society Annual Meeting, Phoenix, 2012.

The formulation of the present invention was administered over a period of 14 days, twice per day, and after the test period less glial activation and reduced apoptosis in all retinal layers of the treated animals with bosentan was observed.

Glial activation (or reactive gliosis) is the inflammatory response of glial cells (neuron support cells) which occurs when there is a noxa (e.g., diabetes) that damages the retina. Neuronal death by apoptosis represents the final stage of the neurodegenerative process of the retina.

This means that the topical administration of bosentan prevents retinal neuroinflammation and neuronal death induced by diabetes.

Surprisingly, the topical ophthalmic formulation of the present invention allows bosentan to reach the retina through the ophthalmic mucosa and to exert its therapeutic action of preventing and/or treating the retinal neurodegeneration.

Some examples are included below to illustrate the present invention but they should not be considered as limiting thereof.

EXAMPLES

The corresponding data to assays with animals are presented as mean±standard deviation. Comparisons of continuous variables were performed using the paired and unpaired Student t-test. Comparisons of categorical variables were performed using Fishers exact test. The levels of statistical significance were set at $p<0.05$.

Example 1: Topical Ophthalmic Formulation

In 75 mL of deionized water 20 g of Cremophor® RH40 were dissolved by magnetic stirring, were left under stirring until completely dissolved. Then 1.5 g of trometamol were added and stirred for 15 minutes, achieving the complete dissolution. An amount of bosentan monohydrate equivalent to 0.5 g of bosentan was immediately added, and left under stirring for 15 minutes, achieving complete dissolution. 2 g of glycine and 1 g of boric acid were then added and left under stirring until completely dissolved.

The solution is brought to a volume of 100 mL by adding deionized water in a sufficient quantity. The solution was filtered through filter paper, and a clear, colourless solution with a pH of 8.06 was obtained. The solution was packed in eye drop dropper bottles with a volume of 5 mL.

Examples 2 to 7: Ophthalmic Topical Compositions

Following a procedure analogous to Example 1, the ophthalmic topical compositions as described in Table 1 were prepared:

TABLE 1

| Component | \multicolumn{6}{c}{Examples} | | | | | |
|---|---|---|---|---|---|---|
| | 2 | 3 | 4 | 5 | 6 | 7 |
| Bosentan | 0.5 | 0.5 | 0.5 | 0.5 | 0.5 | 0.5 |
| PEG 4000 | 20 | — | 20 | 20 | 20 | 15 |
| Propylene glycol | — | 20 | — | — | — | 7.5 |
| Trometamol | — | 1.5 | — | — | — | 1.5 |
| Arginine | 1.5 | — | — | — | — | — |
| Lysine | — | — | — | 1.5 | — | — |
| Methylglucamine | — | — | — | — | 1.5 | — |
| Boric acid | 1 | 1 | — | 1 | 1 | 1 |
| Glycine | 2 | 2 | — | 2 | 2 | 2 |
| Citric acid/sodium citrate | — | — | q.s. pH 4-8.5 | — | — | — |
| Water q.s. | 100 | 100 | 100 | 100 | 100 | 100 |

The amounts of the components are expressed in grams, and the amount of water is referred to 100 mL.

In all cases clear and colourless compositions with a pH between 5 and 8.5 were obtained.

Examples 8 to 25: Excipient Combination

Following a procedure analogous to Example 1, the ophthalmic topical compositions as described in Table 2, 3 and 4 were prepared:

TABLE 2

| Component | \multicolumn{6}{c}{Examples} | | | | | |
|---|---|---|---|---|---|---|
| | 8 | 9 | 10 | 11 | 12 | 13 |
| Bosentan | 0.5 | 0.5 | 0.5 | 0.5 | 0.5 | 0.5 |
| PEG 400 | 20 | — | — | — | 14 | 12 |
| PEG 800 | — | 20 | — | — | — | — |
| PEG 1000 | — | — | 20 | — | — | — |
| PEG 4000 | — | — | — | 20 | — | — |
| Propylene glycol | — | — | — | — | 7 | 8 |
| Trometamol | 0.2 | 0.5 | 1 | 5 | 0.2 | 0.5 |
| Arginine | 5 | 0.2 | 0.5 | 1 | 5 | 0.2 |
| Lysine | 1 | 5 | 0.2 | 0.5 | 1 | 5 |
| Methylglucamine | 0.5 | 1 | 0.5 | 0.2 | 0.5 | 1 |
| Water q.s. | 100 | 100 | 100 | 100 | 100 | 100 |

TABLE 3

| Component | \multicolumn{6}{c}{Examples} | | | | | |
|---|---|---|---|---|---|---|
| | 14 | 15 | 16 | 17 | 18 | 19 |
| Bosentan | 0.5 | 0.5 | 0.5 | 0.5 | 0.5 | 0.5 |
| PEG 400 | 10 | 8 | — | — | — | — |
| Glycerine | — | — | 6 | 8 | 10 | 12 |
| Propylene glycol | 10 | 12 | 14 | 12 | 10 | 8 |
| Trometamol | 1 | 5 | 0.2 | 0.5 | 1 | 5 |
| Arginine | 0.5 | 1 | 5 | 0.2 | 0.5 | 1 |
| Lysine | 0.2 | 0.5 | 1 | 5 | 0.2 | 0.5 |
| Methylglucamine | 0.5 | 0.2 | 0.5 | 1 | 0.5 | 0.2 |
| Water q.s. | 100 | 100 | 100 | 100 | 100 | 100 |

TABLE 4

| Component | Examples | | | | | |
|---|---|---|---|---|---|---|
| | 20 | 21 | 22 | 23 | 24 | 25 |
| Bosentan | 0.5 | 0.5 | 0.5 | 0.5 | 0.5 | 0.5 |
| Cremophor ® RH40 | 20 | 20 | 25 | 20 | 20 | 20 |
| Trometamol | 1 | 1.5 | 0.7 | 1 | — | 1 |
| Glycerine | 2 | 3 | 2 | 2 | 2 | 2 |
| Glycine | — | — | — | — | — | 1 |
| Arginine | — | — | — | — | 2 | — |
| Chlorobutanol | 0.5 | 0.6 | 0.5 | 0.5 | 0.5 | 0.5 |
| Phenylethyl alcohol | 0.5 | 0.6 | 0.5 | 0.5 | 0.5 | 0.5 |
| Citric acid | q.s. pH = 8 | q.s. pH = 8 | q.s. pH = 8.5 | — | — | — |
| Citric acid/sodium citrate | — | — | — | q.s. pH = 8 | q.s. pH = 7.5 | q.s. pH = 8.5 |
| Water q.s. | 100 | 100 | 100 | 100 | 100 | 100 |

Examples 26 to 30: Lipophilic Ointments

Following a standard procedure ophthalmic topical compositions in the form of lipophilic ointments as described in Table 5 were prepared:

TABLE 5

| Component | \multicolumn{5}{c}{Examples} | | | | |
|---|---|---|---|---|---|
| | 26 | 27 | 28 | 29 | 30 |
| Bosentan | 0.5 | 0.5 | 0.5 | 0.5 | 0.5 |
| Liquid Paraffin | 80 | 70 | 75 | 80 | 60 |
| Paraffin | 16 | 26 | 20 | 15 | 34.5 |
| Arginine | 1.5 | 1.5 | 1.5 | 1.5 | 1.5 |
| Glycine | 2 | 2 | 3 | 3 | 5 |

Examples 31 to 35: Hydrophilic Ointments

Following a standard procedure ophthalmic topical compositions in the form of hydrophilic ointments as described in Table 6 were prepared:

TABLE 6

| Component | \multicolumn{5}{c}{Examples} | | | | |
|---|---|---|---|---|---|
| | 31 | 32 | 33 | 34 | 35 |
| Bosentan | 0.5 | 0.5 | 0.5 | 0.5 | 0.5 |
| PEG 4000 | 50 | 60 | 46 | 36 | 50 |
| PEG 400 | 46 | 36 | 50 | 60 | 49.5 |
| Arginine | 1.5 | 1.5 | 3.5 | — | — |
| Glycine | 2 | 2 | — | 3.5 | — |

Examples 36 to 40: Hydrogels

Following a standard procedure ophthalmic topical compositions in the form of hydrogels as described in Table 7 were prepared:

TABLE 7

| Component | \multicolumn{5}{c}{Examples} | | | | |
|---|---|---|---|---|---|
| | 36 | 37 | 38 | 39 | 40 |
| Bosentan | 0.5 | 0.5 | 0.5 | 0.5 | 0.5 |
| HPMC 5 KM | 1 | 2 | 3 | 2 | 1 |
| Arginine | 1.5 | 1.5 | — | 1.5 | 1.5 |

TABLE 7-continued

| Component | Examples | | | | |
|---|---|---|---|---|---|
| | 36 | 37 | 38 | 39 | 40 |
| Trometamol | 1.5 | — | 1.5 | — | — |
| Glycine | 2 | 2 | — | 2 | 2 |
| citric acid/sodium citrate | q.s. pH = 8.5 | q.s. pH = 7 | q.s. pH = 7.5 | q.s. pH = 8 | q.s. pH = 8.5 |
| Water | q.s. 100 g | q.s. 100 g | q.s. 100 g | q.s. 100 g | q.s. 100 g |

Example 41: Ophthalmic Topical Solution with Bosentan Nanoparticles

Nanoparticles were prepared by the solvent evaporation technique.

A 120 mg solution of PLGA 50:50 in 60 mL of ethyl acetate was prepared. To this solution an aqueous solution of 50 mL of water with 12 mg of bosentan monohydrate and 0.5 mg of polyvinyl alcohol under turbo-stirring was incorporated. The resulting mixture was left under continuous agitation and under vacuum for 2 hours. The resulting preparation was then ultracentrifuged and washed with water three times to remove the nanoparticles from the medium.

The nanoparticles were dried in a vacuum oven and, after evaluation, the sufficient amount for a concentration of 0.5 mg/100 mL bosentan monohydrate was dispersed in an isotonic aqueous solution.

Example 42: Ophthalmic Topical Solution with Bosentan Niosomes

Niosomes were prepared by the thin film hydration technique.

Polyoxyethylenated sorbitan monostearate with 20 moles of ethylene oxide, cholesterol and dicetyl phosphate were mixed in a molar ratio 1:0.5:0.1 in a round bottom flask with 10 mL of chloroform.

It was left at 60° C. and under reduced pressure on a rotary evaporator at 120 rpm until complete evaporation.

The thin film formed in the flask was hydrated with 12 mL of pH 7.4 phosphate buffer containing 5 mg of bosentan monohydrate.

The niosome suspension was left to cool 12 h at 4° C. and then filtered through a 0.22 μm nylon filter.

Example 43: Treatment with the Topical Ophthalmic Formulation

In tests 12 male db/db mice aged 10 weeks (Harlan Laboratories, Inc.) were used, and were divided into two groups: 6 of these mice were treated with a formulation of the present invention, and 6 mice with a sodium chloride solution, as described below. 6 non-diabetic (db/+) mice matched by age were also used as the control group.

A drop (5 μl) of the formulation of Example 1 or a drop of vehicle (5 μl of a solution of sodium chloride 0.9% w/v) were administered directly onto the superior corneal surface of each eye of the 12 db/db mice using a syringe, twice daily for 14 days.

On day 15, approximately 1 hour before necropsy, a drop of formulation of the present invention or vehicle was instilled in the eyes of the animals. Following euthanasia, eyes were enucleated. The neuroretina from one of the eyes was extracted, frozen in liquid nitrogen and stored at a temperature of −80° C. The other eye was fixed with a solution of 4% paraformaldehyde, processed routinely, and embedded in paraffin blocks.

Example 44: Determination of the Glial Activation

Glial activation was evaluated by Laser Scanning Confocal microscopy using specific antibodies against GFAP (glial fibrillary acidic protein). Retina sections were fixed in acidic methanol at −20° C. for 2 min, followed by three washes with phosphate buffer (PBS) for 5 min each. Retina sections were permeabilized with a tris buffer (TBS) with 0.025% Triton® X-100 and incubated for 2 hours at room temperature in a blocker solution composed of 1% BSA (serum albumin bovine) and 10% goat serum in 10% PBS. Retina sections were incubated with rabbit anti-GFAP antibody (Abcam Ltd, Cambridge, UK; 1:500 dilution prepared in blocking solution) overnight at 4° C. in a humid atmosphere. After three washes with PBS solution, 5 minutes each, the retina sections were incubated with the secondary antibody Alexa 488 goat anti-rabbit (Invitrogen, San Diego Calif., USA) at a 1:200 dilution prepared in blocking solution. Retina sections were washed three times with PBS, counterstained with Hoechst, mounted with Mounting Medium Fluorescence (Prolong, Invitrogen) and mounted with a coverslip. Comparative digital images from samples were recorded with FluoView FV 1000 Laser Scanning Confocal microscope Olympus using identical settings for brightness and contrast.

A scoring system based on the extent of GFAP staining described in Anderson et al., *Glial and endothelial blood-retinal barrier responses to amyloid-β in the neural retina of the rat*, Olin. Ophthalmol., 2008, 2, 801-816, was used in order to assess the degree of glial activation. This scoring system was as follows:
- Score 1: Müller cell endfeet/ ganglion retinal cell layer (GCL) only;
- Score 2: Müller cell endfeet region/GCL plus a few proximal processes;
- Score 3: Müller cell endfeet plus many processes, but not extending to the outer nuclear layer (ONL) of the retina;
- Score 4: Müller cell endfeet plus processes throughout with some in the ONL;
- Score 5: Müller cell endfeet plus lots of dark processes from GCL to outer margin of ONL.

The score was assessed on the retina of each animal and a minimum of 10 sections per retina.

In Table 8 the degree of glial activation (percentage for each score of GFAP expression) for the three kind of animals shown (control, db/db treated with vehicle, and db/db treated with bosentan) is shown:

TABLE 8

| Score | Control (db/+) | Vehicle (db/db) | Bosentan (db/db) |
|---|---|---|---|
| 1 | 95 | 0 | 85 |
| 2 | 5 | 0 | 15 |
| 3 | 0 | 59 | 0 |
| 4 | 0 | 40 | 0 |
| 5 | 0 | 1 | 0 |

It is shown that, as expected, in non-diabetic animals, GFAP expression was largely confined to the ganglion retinal cell layer (GCL) and, therefore, the GFAP score was ≤2.

Vehicle-treated diabetic animals showed a significantly increased expression of GFAP than non-diabetic mice matched by age. Thus, 100% of diabetic animals had a GFAP score ≥3, reaching a considerable part of them (40%) a score of 4. The administration of bosentan for two weeks resulted in a significant decrease of reactive gliosis, and GFAP score of the animals treated with bosentan was <3 in all cases, with a large majority (85%) less than 2.

Therefore, it is proved the efficacy of the formulation of the present invention to reduce glial activation.

Example 45: Immunohistochemical Analysis for Evaluation of Apoptosis

Immunohistochemical analysis for apoptosis assessment was carried out TUNEL (Terminal Transferase dUTP Nick-End Labeling) staining using the DeadEnd Fluorometric TUNEL System Kit (Promega, Madison, Wis., USA).

Cryosections of retina were permeabilized by incubation on ice for 2 min with 0.1% Triton X-100 and 0.1% sodium citrate freshly prepared solution. The secondary antibody was Alexa 488 goat anti-rabbit (Invitrogen, San Diego Calif., USA). For evaluation by Laser Scanning Confocal microscopy, the excitation wavelength was 488 nm and detection in the range from 515 to 565 nm, which corresponds to green colour.

The evaluation was carried out in the retina of each animal and a minimum of 10 sections per retina.

Table 9 shows the results corresponding to TUNEL staining-positive cell percentage in the different layers of the retina. The mean values and standard deviation for the percentages for each layer of retina (outer nuclear layer, ONL; inner nuclear layer, INL: ganglion cell layer, GCL) are shown in parentheses:

TABLE 9

| Retinal layer | Control (db/+) | Vehicle (db/db) | Bosentan (db/db) |
|---|---|---|---|
| ONL | 0.01 (0.00) | 30.85 (2.16) | 0 (0.07) |
| INL | 0.01 (0.00) | 8.15 (2.10) | 0.36 (0.31) |
| GCL | 0.01 (0.00) | 36.49 (5.46) | 1.42 (0.38) |

In this table it is shown that the apoptosis rate in all layers of the retina of animals treated with the formulation of the present invention was similar to the rate of control animals (non-diabetic), and significantly lower than the vehicle-treated diabetic animals. Statistical significance wasp <0.001.

Therefore, it has been found that the administration of the formulation of the present invention to diabetic animals for two weeks led to a significant prevention of apoptosis in all retinal layers.

The invention claimed is:

1. A method for preventing and/or treating retinal neurodegeneration induced by diabetes and/or aging, the method comprising administering directly to the eye of a subject in need thereof a therapeutically effective amount of the topical ophthalmic formulation comprising:
    1) between 0.1% and 5.0% (w/v) of bosentan;
    2 between 1% and 49% (w/v) of the solubilizer polyoxyethylenated derivatives of castor oil;
    3 between 0.5% and 20% (w/v) of glycine; and
    4 between 0.1% and 25% (w/v) of an amine selected from the group consisting of trometamol, arginine, lysine, methylglucamine, and mixtures thereof,
    wherein the pH of the aqueous solution is between 3.5 and 10.5, and the percentages (w/v) are expressed with respect to the total volume of the formulation.

2. The method of claim 1, wherein the retinal neurodegeneration is early stage retinal neurodegeneration.

3. The method of claim 1, wherein the topical ophthalmic formulation is a solution, suspension, emulsion, colloidal system, ointment, unguent, gel, or ophthalmic implant.

4. The method of claim 3, wherein the topical ophthalmic formulation is an aqueous solution.

5. The method according to claim 1, wherein the formulation is in a liquid, semisolid, or solid pharmaceutical form.

6. The method according to claim 5, wherein the formulation is an aqueous solution.

7. The method according to claim 1, wherein the topical ophthalmic formulation further comprises an additional active ingredient selected from the group consisting of corticoids, prostaglandins, growth factors, anti-VEGF factors, and peptides.

8. The method according to claim 1, wherein the topical ophthalmic formulation further comprises one or more compounds selected from the group consisting of surfactants, cosolvents, viscosifying agents, preservatives, isotonizing agents, isoosmotizing agents, absorption enhancers of the active ingredient, mucoadhesive polymers, non-mucoadhesive polymers, chelants, stabilizers, antioxidants, and mixtures thereof.

9. The method according to claim 1, wherein the bosentan is incorporated in the form of microparticles, nanoparticles, liposomes, or niosomes.

10. The method of claim 1, wherein the topical ophthalmic formulation further comprises between 0.1% and 10% (w/v) of boric acid.

* * * * *